United States Patent
Lim et al.

(10) Patent No.: US 9,283,110 B2
(45) Date of Patent: Mar. 15, 2016

(54) PATIENT TEMPERATURE CONTROL CATHETER WITH OUTER SLEEVE COOLED BY INNER SLEEVE

(71) Applicant: ZOLL CIRCULATION, INC., Sunnyvale, CA (US)

(72) Inventors: Alex L. Lim, Santa Clara, CA (US); Venkata Vishnu Gurukula, Mountain View, CA (US); Jeremy T. Dabrowiak, Redwood City, CA (US); Richard A. Helkowski, Redwood City, CA (US)

(73) Assignee: Zoll Circulation, Inc., San Jose, CA (US)

( * ) Notice: Subject to any disclaimer, the term of this patent is extended or adjusted under 35 U.S.C. 154(b) by 311 days.

(21) Appl. No.: 13/622,104

(22) Filed: Sep. 18, 2012

(65) Prior Publication Data

US 2013/0073014 A1     Mar. 21, 2013

Related U.S. Application Data

(60) Provisional application No. 61/536,668, filed on Sep. 20, 2011.

(51) Int. Cl.
*A61F 7/12* (2006.01)
*A61B 18/02* (2006.01)
*A61F 7/00* (2006.01)

(52) U.S. Cl.
CPC ............... *A61F 7/12* (2013.01); *A61F 7/0085* (2013.01); *A61F 2007/0054* (2013.01); *A61F 2007/0056* (2013.01); *A61F 2007/0094* (2013.01); *A61F 2007/0096* (2013.01); *A61F 2007/126* (2013.01)

(58) Field of Classification Search
CPC ... A61F 7/00; A61F 7/105; A61F 2007/0054; A61F 2007/0056; A61F 2007/126; A61F 7/0085; A61F 7/12; A61B 2018/02; A61B 2018/0293; A61B 2018/0005–2018/00047; A61B 2018/00023
USPC .................. 606/21–26; 607/105, 113, 22–26
See application file for complete search history.

(56) References Cited

U.S. PATENT DOCUMENTS

| 1,459,112 A | 6/1923 | Mehl |
| 1,857,031 A | 5/1932 | Schaffer |

(Continued)

FOREIGN PATENT DOCUMENTS

| DE | 19531935 | 2/1997 |
| GB | 2040169 | 8/1980 |

(Continued)

OTHER PUBLICATIONS

F.W. Behmann, E. Bontke, "Die Regelung der Wärmebildung bei künstlicher Hypothermie", Pflügers Archie, Bd. 266, S. 408-421 (1958).

(Continued)

*Primary Examiner* — Linda Dvorak
*Assistant Examiner* — Yasamin Ekrami
(74) *Attorney, Agent, or Firm* — John L. Rogitz

(57) ABSTRACT

A catheter has an inner sleeve through which refrigerant circulates to and from a source of refrigerant. The catheter also has an outer sleeve surrounding the inner sleeve, including a distal end thereof. The outer sleeve is filled with a frozen biocompatible substance. The refrigerant is separated from the biocompatible substance by one or more walls of the inner sleeve such that the refrigerant is isolated from a patient in whom the catheter is positioned by both the inner sleeve and the frozen biocompatible substance. The refrigerant circulates through the catheter when the catheter is positioned in the patient to maintain the biocompatible substance frozen as heat is transferred from the patient to the biocompatible substance.

13 Claims, 6 Drawing Sheets

(56) References Cited

U.S. PATENT DOCUMENTS

| | | |
|---|---|---|
| 2,663,030 A | 12/1953 | Dahlberg |
| 2,673,987 A | 4/1954 | Upshaw et al. |
| 3,225,191 A | 12/1965 | Calhoun |
| 3,369,549 A | 2/1968 | Armao |
| 3,425,419 A | 2/1969 | Dato |
| 3,504,674 A | 4/1970 | Swenson |
| 3,726,269 A | 4/1973 | Webster, Jr. |
| 3,744,555 A | 7/1973 | Fletcher et al. |
| 3,751,077 A | 8/1973 | Hiszpanski |
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress et al. |
| 4,126,132 A | 11/1978 | Portner et al. |
| 4,153,048 A | 5/1979 | Magrini |
| 4,173,228 A | 11/1979 | Van Steenwyk et al. |
| 4,181,132 A | 1/1980 | Parks |
| 4,298,006 A | 11/1981 | Parks |
| 4,459,468 A | 7/1984 | Bailey |
| 4,532,414 A | 7/1985 | Shah et al. |
| 4,554,793 A | 11/1985 | Harding, Jr. |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,906,237 A | 3/1990 | Johansson et al. |
| 4,941,475 A | 7/1990 | Williams et al. |
| 5,092,841 A | 3/1992 | Spears |
| 5,103,360 A | 4/1992 | Maeda |
| 5,106,360 A | 4/1992 | Ishiwara et al. |
| 5,192,274 A | 3/1993 | Bierman |
| 5,195,965 A | 3/1993 | Shantha |
| 5,211,631 A | 5/1993 | Sheaff |
| 5,269,758 A | 12/1993 | Taheri |
| 5,281,215 A | 1/1994 | Milder |
| 5,304,214 A | 4/1994 | DeFord et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,403,281 A | 4/1995 | O'Neill et al. |
| 5,433,740 A | 7/1995 | Yamaguchi |
| 5,437,673 A | 8/1995 | Baust et al. |
| 5,458,639 A | 10/1995 | Tsukashima et al. |
| 5,486,207 A | 1/1996 | Mahawili |
| 5,486,208 A | 1/1996 | Ginsburg |
| 5,501,681 A | 3/1996 | Neuwirth et al. |
| 5,507,792 A | 4/1996 | Mason et al. |
| 5,531,714 A | 7/1996 | Dahn et al. |
| 5,531,776 A | 7/1996 | Ward et al. |
| 5,624,392 A | 4/1997 | Saab |
| 5,634,907 A | 6/1997 | Rani et al. |
| 5,676,670 A | 10/1997 | Kim |
| 5,701,905 A | 12/1997 | Esch |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,776,079 A | 7/1998 | Cope et al. |
| 5,788,647 A | 8/1998 | Eggers |
| 5,837,003 A | 11/1998 | Ginsburg |
| 5,862,675 A | 1/1999 | Scaringe et al. |
| 5,895,418 A | 4/1999 | Saringer |
| 5,908,407 A | 6/1999 | Frazee et al. |
| 5,957,963 A | 9/1999 | Dobak, III |
| 5,980,561 A | 11/1999 | Kolen et al. |
| 6,019,783 A | 2/2000 | Philips et al. |
| 6,042,559 A | 3/2000 | Dobak, III |
| 6,051,019 A | 4/2000 | Dobak, III |
| 6,059,825 A | 5/2000 | Hobbs et al. |
| 6,096,068 A | 8/2000 | Dobak, III et al. |
| 6,110,139 A | 8/2000 | Loubser |
| 6,117,065 A | 9/2000 | Hastings et al. |
| 6,117,105 A | 9/2000 | Bresnaham et al. |
| 6,124,452 A | 9/2000 | Di Magno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,677 A | 11/2000 | Dobak, III |
| 6,231,594 B1 | 5/2001 | Dae |
| 6,283,940 B1 | 9/2001 | Mulholland |
| 6,299,599 B1 | 10/2001 | Pham et al. |
| 6,338,727 B1 | 1/2002 | Noda et al. |
| 6,364,899 B1 * | 4/2002 | Dobak, III .................. 607/113 |
| 6,383,144 B1 | 5/2002 | Mooney et al. |
| 6,409,747 B1 | 6/2002 | Gobin et al. |
| 6,416,533 B1 | 7/2002 | Gobin et al. |
| 6,428,563 B1 | 8/2002 | Keller |
| 6,450,990 B1 | 9/2002 | Walker et al. |
| 6,464,716 B1 | 10/2002 | Dobak, III et al. |
| 6,468,297 B1 | 10/2002 | Williams et al. |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | Le Pivert |
| 6,554,791 B1 | 4/2003 | Cartledge et al. |
| 6,605,106 B2 | 8/2003 | Schwartz |
| 6,610,083 B2 | 8/2003 | Keller et al. |
| 6,620,187 B2 | 9/2003 | Carson et al. |
| 6,620,188 B1 | 9/2003 | Ginsburg et al. |
| 6,624,679 B2 | 9/2003 | Tomaivolo et al. |
| 6,635,079 B2 | 10/2003 | Unsworth et al. |
| 6,679,906 B2 | 1/2004 | Hammack et al. |
| 6,685,733 B1 | 2/2004 | Dae et al. |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,740,109 B2 | 5/2004 | Dobak, III |
| 6,799,342 B1 | 10/2004 | Jarmon |
| 6,843,800 B1 | 1/2005 | Dobak, III |
| 6,887,263 B2 | 5/2005 | Bleam et al. |
| 6,893,419 B2 | 5/2005 | Noda et al. |
| 6,969,399 B2 | 11/2005 | Schock et al. |
| 7,195,625 B2 * | 3/2007 | Lentz ........................ 606/21 |
| 7,473,251 B2 * | 1/2009 | Knowlton et al. .......... 606/41 |
| 7,510,569 B2 | 3/2009 | Dae et al. |
| 7,666,215 B2 | 2/2010 | Callister et al. |
| 7,822,485 B2 | 10/2010 | Collins |
| 7,846,193 B2 | 12/2010 | Dae et al. |
| 7,857,781 B2 | 12/2010 | Noda et al. |
| 8,012,147 B2 * | 9/2011 | Lafontaine .................. 606/21 |
| 8,043,283 B2 * | 10/2011 | Dobak et al. ............... 606/23 |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 8,211,095 B2 * | 7/2012 | Gowda et al. .............. 606/16 |
| 2001/0031946 A1 | 10/2001 | Walker et al. |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0032438 A1 | 3/2002 | Lafontaine |
| 2002/0091378 A1 | 7/2002 | Dobak et al. |
| 2002/0145525 A1 | 10/2002 | Friedman et al. |
| 2002/0177804 A1 * | 11/2002 | Saab ........................ 604/45 |
| 2002/0183692 A1 | 12/2002 | Callister |
| 2002/0198579 A1 | 12/2002 | Khanna |
| 2003/0236496 A1 | 12/2003 | Samson et al. |
| 2004/0034344 A1 * | 2/2004 | Ryba ........................ 606/21 |

(56) References Cited

U.S. PATENT DOCUMENTS

| | | |
|---|---|---|
| 2004/0089058 A1 | 5/2004 | De Haan et al. |
| 2004/0102825 A1 | 5/2004 | Daoud |
| 2004/0143312 A1* | 7/2004 | Samson et al. ............ 607/105 |
| 2004/0210231 A1 | 10/2004 | Boucher et al. |
| 2004/0243117 A1 | 12/2004 | Lentz |
| 2005/0156744 A1 | 7/2005 | Pires |
| 2007/0007640 A1 | 1/2007 | Harnden et al. |
| 2007/0076401 A1 | 4/2007 | Carrez et al. |
| 2008/0033414 A1* | 2/2008 | Levin et al. ............... 606/21 |
| 2008/0065179 A1* | 3/2008 | Yon et al. ................. 607/105 |
| 2008/0161890 A1* | 7/2008 | Lafontaine ............... 607/105 |
| 2009/0234345 A1* | 9/2009 | Hon ........................... 606/21 |
| 2009/0287201 A1* | 11/2009 | Lalonde et al. ........... 606/21 |
| 2009/0299358 A1* | 12/2009 | Lafontaine ................ 606/21 |
| 2011/0028938 A1* | 2/2011 | Barbut et al. ............. 604/514 |
| 2011/0178514 A1* | 7/2011 | Levin et al. ............... 606/23 |

FOREIGN PATENT DOCUMENTS

| | | |
|---|---|---|
| GB | 1183185 | 2/1985 |
| GB | 2212262 | 7/1989 |
| GB | 2383828 | 7/2003 |
| JP | 09-215754 | 8/1997 |
| JP | 10-0127777 | 5/1998 |
| JP | 10-305103 | 11/1998 |
| WO | 9001682 | 2/1990 |
| WO | 9304727 | 3/1993 |
| WO | 9400177 | 1/1994 |
| WO | 9401177 | 1/1994 |
| WO | 9725011 | 7/1997 |
| WO | 9824491 | 6/1998 |
| WO | 9840017 | 9/1998 |
| WO | 9965410 A1 | 12/1999 |
| WO | 0010494 | 3/2000 |
| WO | 0047118 A1 | 8/2000 |
| WO | 0113809 | 3/2001 |
| WO | 0164146 | 9/2001 |
| WO | 0176517 | 10/2001 |
| WO | 0183001 | 11/2001 |

OTHER PUBLICATIONS

F.W. Behmann, E. Bontke, "Intravasale Kühlung", Pffügers Archie, Bd. 263, S. 145-165 (1956).

Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.

Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, Vo. 44, No. 5 (1998).

* cited by examiner

| List of Refrigerant and Detail |
|---|
| Preferred:    - $CO_2$ (R-744) as a fluid or supercritical fluid.<br>            - Latent heat ≅570 kj/kg<br>               needs ~8 liters to maintain a 500 watt system for 2 hours continuous application. |
| Others:      - Freon (R12 or R22) (phased out)<br>               latent heat ≅240 kj/kg 16-20 liters.<br>           - R-410a (Freon replacement)<br>               latent heat ≅240 kj/kg 16-20 liters.<br>           - R-134a (Freon replacement)<br>               latent heat ≅240 kj/kg 16-20 liters.<br>           - N2 (very low boiling point -212°)<br>               latent heat ≅200 kj/kg<br>               ~22 liters for 500 watt system for 2 hours. |

*FIG. 7*

Ventable System- May Be Subject to Environmental Regulation

Closed-Loop: Systems-Most Expensive and Most Technologically Challenging

PATIENT TEMPERATURE CONTROL CATHETER WITH OUTER SLEEVE COOLED BY INNER SLEEVE

FIELD OF THE INVENTION

The present application relates generally to patient temperature control systems.

BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, it might be desirable to rewarm a hypothermic patient.

As recognized by the present application, the above-mentioned advantages in regulating temperature can be realized by cooling or heating the patients entire body using a closed loop heat exchange catheter placed in the patient's venous system and circulating a working fluid such as saline through the catheter, heating or cooling the working fluid as appropriate in an external heat exchanger that is connected to the catheter. The following U.S. patents, all of which are incorporated herein by reference, disclose various intravascular catheters/systems/methods for such purposes: U.S. Pat. No. 6,881,551 and U.S. Pat. No. 6,585,692 (tri-lobe catheter), U.S. Pat. No. 6,551,349 and U.S. Pat. No. 6,554,797 (metal catheter with bellows), U.S. Pat. No. 6,749,625 and U.S. Pat. No. 6,796,995 (catheters with non-straight, non-helical heat exchange elements), U.S. Pat. No. 6,126,684, U.S. Pat. No. 6,299,599, U.S. Pat. No. 6,368,304, and U.S. Pat. No. 6,338,727 (catheters with multiple heat exchange balloons), U.S. Pat. No. 6,146,411, U.S. Pat. No. 6,019,783, U.S. Pat. No. 6,581,403, U.S. Pat. No. 7,287,398, and U.S. Pat. No. 5,837,003 (heat exchange systems for catheter), U.S. Pat. No. 7,857,781 (various heat exchange catheters).

SUMMARY OF THE INVENTION

Accordingly, a catheter includes an inner sleeve through which refrigerant, which may be supercritical, circulates to and from a source of refrigerant and an outer sleeve surrounding the inner sleeve. The catheter has both a proximal end and distal end relative to the source of the refrigerant. The outer sleeve is filled with a biocompatible substance, which may be frozen in non-limiting embodiments. Additionally, the refrigerant is separated from the biocompatible substance by one or more walls of the inner sleeve such that the refrigerant is isolated from a patient in whom the catheter is positioned by both the inner sleeve and the frozen biocompatible substance. Refrigerant may thus circulate through the catheter when the catheter is positioned in the patient to maintain the biocompatible substance at a designated temperature (e.g., below the freezing temperature/freezing point of the biocompatible substance) as heat is transferred from the patient to the biocompatible substance. The refrigerant may be simply vented to ambient surroundings after cooling the biocompatible substance, or recovered in a storage tank, or recirculated in a closed loop through, e.g., a compressor.

If desired, the refrigerant may be Freon, and the biocompatible substance may be saline or purified water. In non-limiting embodiments, the inner sleeve may be cylindrical. Furthermore, if desired, the outer sleeve may also be generally cylindrical, except at proximal and distal ends of the catheter. Further still, the inner sleeve and outer sleeve of the catheter may be coaxial with each other. Also in some non-limiting embodiments, the inner sleeve may have an opening juxtaposed with a proximal end of the inner sleeve and a closed distal end opposite the proximal end such that refrigerant may enter the inner sleeve only through the proximal end and not pass through the distal end.

In other embodiments the refrigerant is supercritical gas such as $CO_2$ in liquid phase, or liquid Nitrogen, or liquid Helium or other noble gases. For $CO_2$ 8 liters may be used for two hours. A temperature sensor or optical sensor may be in communication with the biocompatible substance to signal when it is at a temperature or state requiring additional cooling. The biocompatible substance may be absent from the outer sleeve upon insertion into the patient so that the device essentially is in a deflated state during insertion, with the biocompatible substance being infused into the outer sleeve after the catheter has been inserted into the patient. A pressure sensor/regulator may be provided for the refrigerant.

If desired, in addition to the above, the catheter may also have at least one refrigerant sensor between the inner sleeve and outer sleeve. The refrigerant sensor may communicate with a control system engaged with the catheter and, responsive to detecting refrigerant between the sleeves, generate a signal to the control system to cause the control system to activate an audible and/or visual alarm if the temperature of the refrigerant deviates outside a designated temperature range.

In another aspect, a method for cooling a patient in whom a catheter is disposed includes disposing a biocompatible fluid in the catheter. The method also includes removing heat from the biocompatible fluid using refrigerant circulating through the catheter. Additionally, the method includes shielding the patient from exposure to the refrigerant at least in part using the biocompatible fluid.

In still another aspect, a system includes a catheter for cooling a patient in whom the catheter is disposed. The system also includes a source of refrigerant in fluid communication with the catheter. The catheter has an inner sleeve through which refrigerant circulates to and from the source of refrigerant. Additionally, the catheter has an outer sleeve surrounding the inner sleeve that includes a distal end and is filled with a biocompatible substance. The refrigerant circulates through the catheter when the catheter is positioned in the patient to maintain the biocompatible substance within a designated temperature range as heat is transferred from the patient to the biocompatible substance.

The details of the present invention, both as to its structure and operation, can best be understood in reference to the accompanying drawings, in which like reference numerals refer to like parts, and in which:

BRIEF DESCRIPTION OF THE DRAWINGS

FIGS. 6-10 illustrate further details.

DETAILED DESCRIPTION OF THE PREFERRED EMBODIMENT

Figure 1:
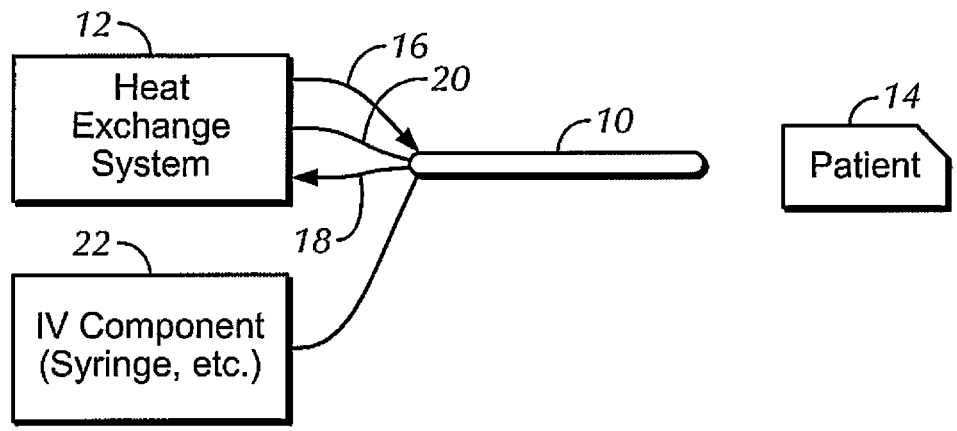
FIG. 1 is a schematic diagram showing an example catheter engaged with an example heat exchange system.

Referring initially to FIG. 1, an intravascular temperature management catheter 10 is in fluid communication with a catheter temperature control system 12 that includes a processor executing logic in accordance with present principles, and as described in one or more of the patents referenced herein, to control the temperature of working fluid circulating through the catheter 10 in accordance with a treatment paradigm responsive to patient core temperature feedback signals. In accordance with present principles, the catheter 10 can be used to induce therapeutic hypothermia in a patient 14 using the catheter, in which coolant such as but not limited to saline circulates in a closed loop, such that no coolant enters the body. Such treatment may be indicated for stroke, cardiac arrest (post-resuscitation), acute myocardial infarction, spinal injury, and traumatic brain injury. The catheter 10 can also be used to warm a patient, e.g., after bypass surgery or burn treatment, and to combat hyperthermia in, e.g., patient suffering from sub-arachnoid hemorrhage or intracerebral hemorrhage.

As shown, working fluid such a refrigerant may be circulated between the heat exchange system 12 and catheter 10 through supply and return lines 16, 18 that connect to the proximal end of the catheter 10 as shown. Note that as used herein, "proximal" and "distal" in reference to the catheter are relative to the system 12. A patient temperature signal from a catheter-borne temperature sensor may be provided to the system 12 through an electrical line 20 or wirelessly if desired. Alternatively, a patient temperature signal may be provided to the system 12 from a separate esophageal probe or rectal probe or tympanic sensor or bladder probe or other temperature probe that measures the temperature of the patient 14.

The catheter 10, in addition to interior supply and return lumens through which the working fluid is circulated, may also have one or more infusion lumens connectable to an IV component 22 such as a syringe or IV bag for infusing medicaments into the patient, or an instrument such as an oxygen or pressure monitor for monitoring patient parameters, etc.

The catheter 10 can be positioned typically in the vasculature of the patient 14 and more preferably in the venous system of the patient 14 such as in the inferior vena cava through a groin insertion point or the superior vena cava through a neck (jugular or subclavian) insertion point.

Figure 2:
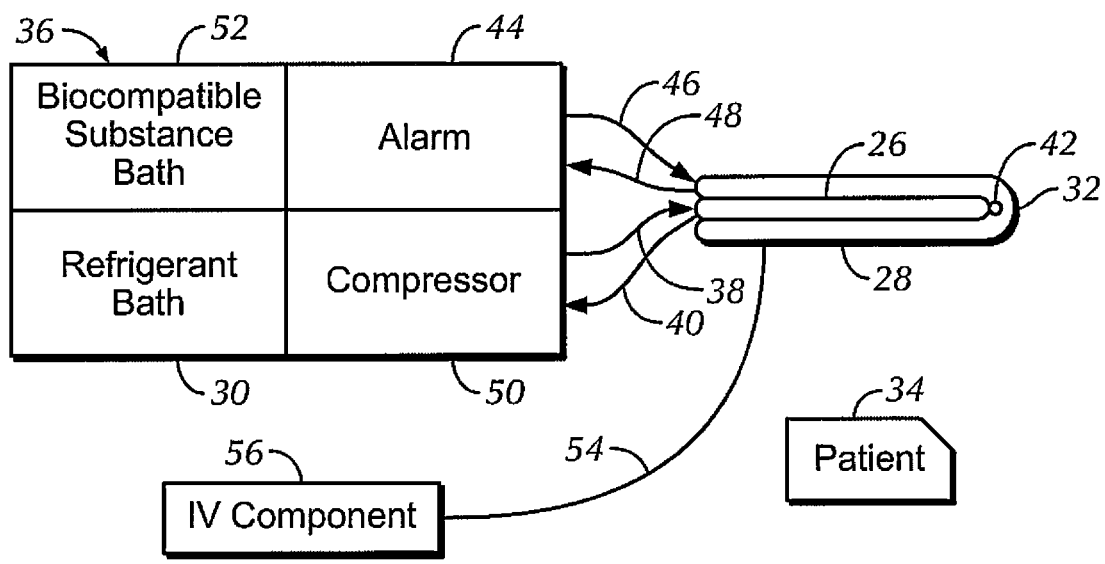
FIG. 2 is a schematic diagram of a catheter having an inner sleeve and an outer sleeve in accordance with present principles.

Now referring to FIG. 2, a schematic diagram of a catheter having an inner sleeve and an outer sleeve is shown. An intravascular temperature management catheter 24 has an inner sleeve 26 through which refrigerant may circulate to and from a source of refrigerant, such as a catheter temperature control system 36 engaged with the catheter as shown in FIG. 2. The refrigerant may be, without limitation, Freon. The catheter also has an outer sleeve 28 substantially surrounding the inner sleeve 26. The outer sleeve 28 includes a distal end 32 and may filled with a biocompatible substance such as, but not limited to, saline. Furthermore, the biocompatible substance may be frozen, if desired. In lieu of saline, in some non-limiting embodiments, the biocompatible substance may be purified water or another substance having a freezing point temperature higher than the freezing point temperature of blood in, e.g., a vein of a patient 34 in which the catheter 24 is disposed.

It may be appreciated from FIG. 2 that the refrigerant may be separated from the biocompatible substance by one or more walls of the inner sleeve 26 such that the refrigerant is isolated from the patient 34 in whom the catheter is to be positioned by both the inner sleeve 26 and the frozen biocompatible substance in the outer sleeve 28. Thus, the refrigerant circulates within the inner sleeve 26 of the catheter 24 to transfer heat through the inner sleeve 26 and away from the biocompatible substance when the catheter 24 is positioned in the patient 34 to maintain the biocompatible substance frozen as heat is transferred from the patient 34 to the biocompatible substance. It is to be understood that the catheter 24 can be positioned typically in the vasculature of the patient 34 and more preferably in the venous system of the patient 34 such as in the inferior vena cava through a groin insertion point or the superior vena cava through a neck (jugular or subclavian) insertion point to transfer heat away from the patient 34.

Still in reference to FIG. 2, the catheter temperature control system 36 (alternatively referenced herein as a heat exchange system) includes a processor executing logic described in one or more of the patents referenced herein. Thus, the control system 36 may control the temperature of the refrigerant circulating through the inner sleeve 26 in accordance with a treatment paradigm responsive to patient core temperature feedback signals as described in further detail below. In accordance with present principles, the catheter 24 can be used to induce therapeutic hypothermia in the patient.

Thus, as also shown in FIG. 2, working fluid may be circulated between the control system 36 and catheter 24 through supply and return lines 38 and 40. It is to be understood that the inner sleeve 26 has an opening(s) juxtaposed with the proximal end of the inner sleeve 26 and a closed distal end opposite the proximal end such that refrigerant may enter the inner sleeve 26 only through the proximal end and cannot pass through the distal end. Note that as used herein, "proximal" and "distal" in reference to the catheter are relative to the control system 36. Thus, the supply and return lines 38 and 40 connect a refrigerant bath 30 on the control system 36 that contains refrigerant to the opening(s) of the proximal end of the catheter 24 as shown such that a compressor 50 may compress (and help circulate) the refrigerant between the bath 30 and inner portion of the catheter 24 defined by the inner sleeve 26. If desired, an additional refrigerant pump may be provided out the outlet of the compressor to pump the refrigerant in the closed loop that includes the catheter, to remove heat from the biocompatible substance.

As shown in FIG. 2, refrigerant sensor 42 may also be included on the catheter 24 between the inner sleeve 26 and outer sleeve 28 to generate a refrigerant detection signal to the control system 36 through an electrical line (not shown), or wirelessly if desired, responsive to detecting refrigerant between the sleeves. Further, in non-limiting embodiments, refrigerant detection signals may be sent at a non-limiting temporal interval, when demanded, when the control system 36 is first powered on, etc. If the signal generated by the sensor 42 indicates that refrigerant is present in the chamber which is supposed to hold only biocompatible fluid, the control system 36 may activate an audible and/or visual alarm 44. In an example embodiment, the sensor 42 is a Freon sensor.

Additionally, it is to be understood that while the biocompatible substance may preferably be frozen while the catheter is positioned in the patient 34, in other non-limiting embodiments the biocompatible substance may optionally be a liquid substance or gaseous substance. Thus, while the outer sleeve 28 of the catheter 24 may be filled with the biocompatible substance and subsequently closed such that no biocompatible substance escapes from the outer sleeve 28 prior to positioning the catheter in the patient 34 (regardless of the current state of the biocompatible substance or whether the biocompatible substance changes states), the biocompatible substance my instead be circulated to transfer heat away from the patient 34. Therefore, in alternative non-limiting embodiments, the biocompatible substance (when in a fluid or gaseous form) may circulate between a biocompatible substance bath 52 on the control system 36 and the catheter 24 through optional supply and return lines 46 and 48. The supply and return lines 46 and 48 may connect to a proximal end portion of the catheter 24 bearing the biocompatible substance as also shown in the non-limiting embodiment of FIG. 2. Additionally, in such an embodiment a substance pump (not shown) may circulate the biocompatible substance between the bath 52 and outer portion of the catheter 24 defined by the inner sleeve 26 and outer sleeve 28.

It may now be appreciated that the biocompatible substance (when a liquid or gas) may also circulate in a closed loop such that biocompatible substance enters the body. It is to be understood that any discharge of the biocompatible substance when frozen similarly does not enter the body. Lastly, the catheter 24, in addition to interior supply and return lumens through which the refrigerant is circulated, may also have one or more infusion lumens 54 connectable to an IV component 56 such as a syringe or IV bag for infusing medicaments into the patient, or an instrument such as an oxygen or pressure monitor for monitoring patient parameters, etc.

Figure 3:
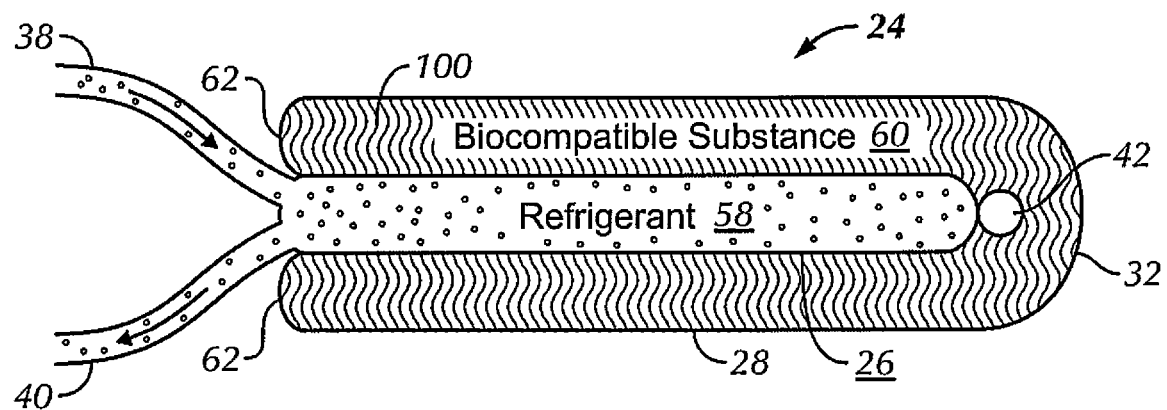
FIG. 3 is a side cross-sectional view of a catheter in accordance with present principles, it being understood that the cross-sections represent refrigerant and biocompatible fluid, which may be frozen.

Now in reference to FIG. 3, a side cross-sectional view of the catheter 24 is shown. The catheter 24 still has the inner sleeve 26, the outer sleeve 28, and the distal end generally designated 32. As may be seen in FIG. 3, the inner sleeve 26 and outer sleeve 28 may be coaxial with each other. FIG. 3 also shows the sensor 42 as described above. Further, the cross-sectional view of FIG. 3 shows refrigerant 58 contained within the inner sleeve 26 and understood to be circulating to and from the control system 36 (not shown in FIG. 3) through refrigerant supply and return lines 38 and 40.

FIG. 3 also shows biocompatible substance 60 contained in the portion of the catheter 24 between the inner sleeve 26 and outer sleeve 28. It may be appreciated from FIG. 3 that, in non-limiting embodiments, closed ends 62 enclose the portion of the catheter 24 between the inner sleeve 26 and outer sleeve 28 containing the biocompatible substance 60. It may therefore be further appreciated that no biocompatible substance 60 may escape from between the inner sleeve 26 and outer sleeve 28.

Figure 4:
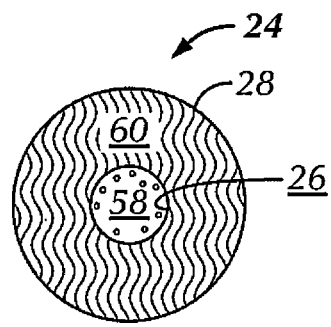
FIG. 4 is a transverse cross-sectional view of a catheter in accordance with present principles.

Moving on to FIG. 4, a transverse cross-sectional view of the catheter 24 described in reference to FIG. 2 is shown. The catheter 24 still has the inner sleeve 26 and outer sleeve 28. FIG. 4 also shows the refrigerant 58 and biocompatible substance 60 referenced above. It may be appreciated from the cross-sectional view of FIG. 4 that, in non-limiting embodiments, the inner sleeve 26 may be generally cylindrical.

Figure 5:
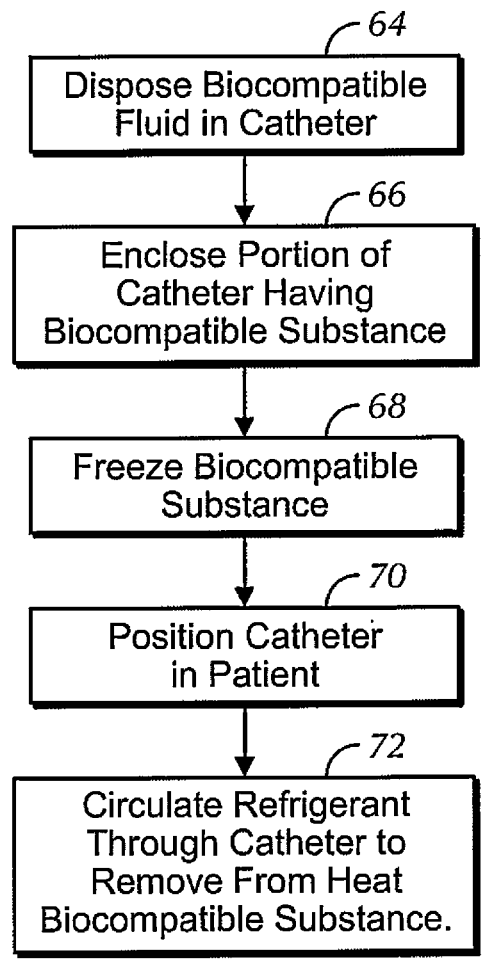
FIG. 5 is a flow chart of non-limiting logic in accordance with present principles.
Figure 6:
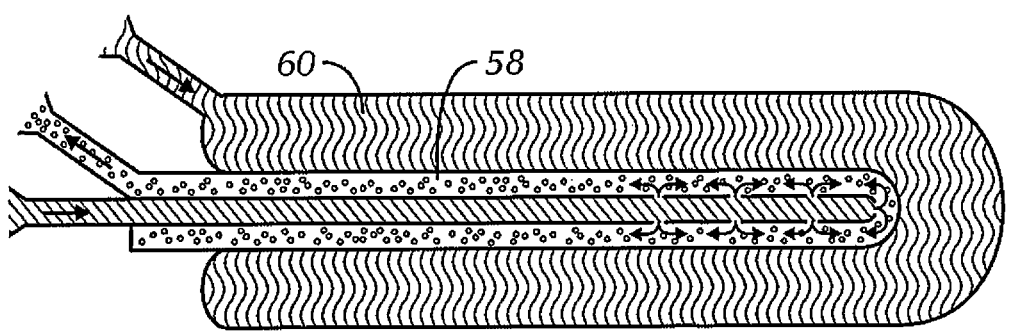
Figure 8:
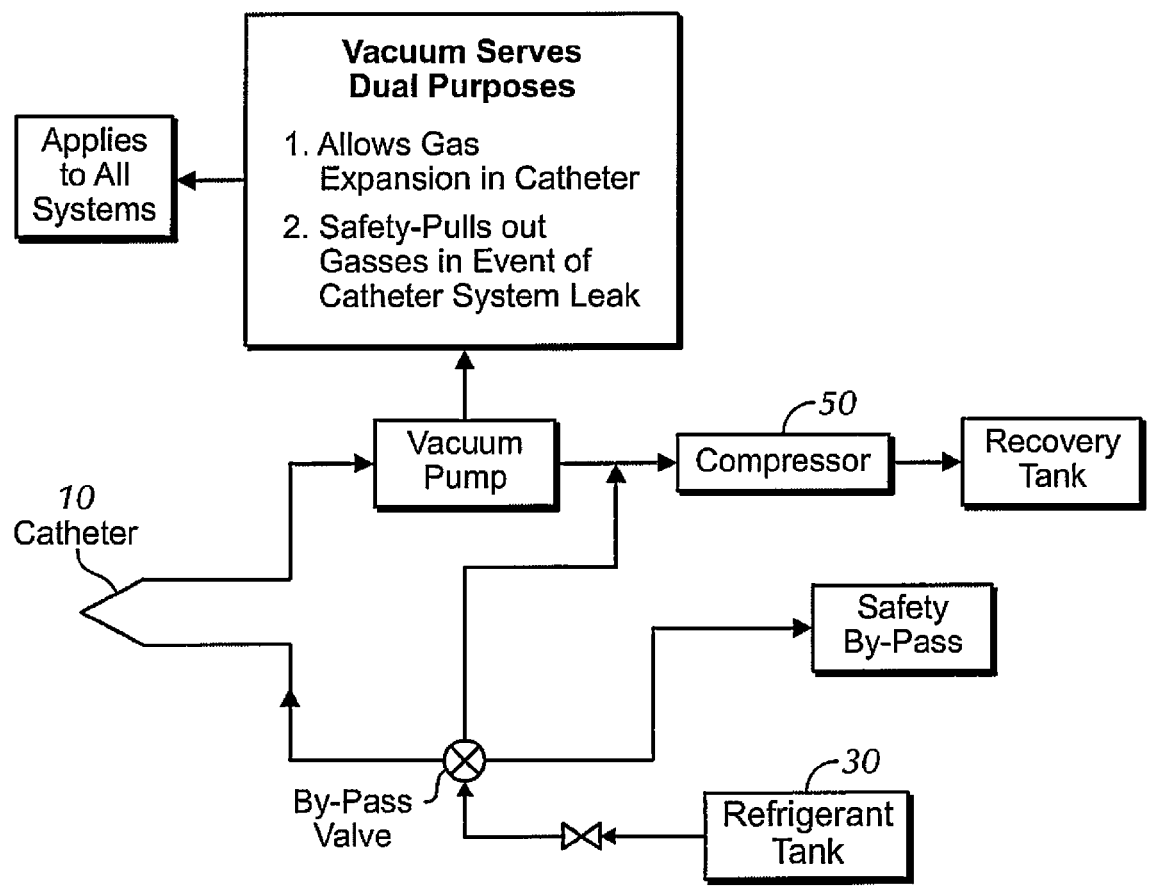
Figure 9:
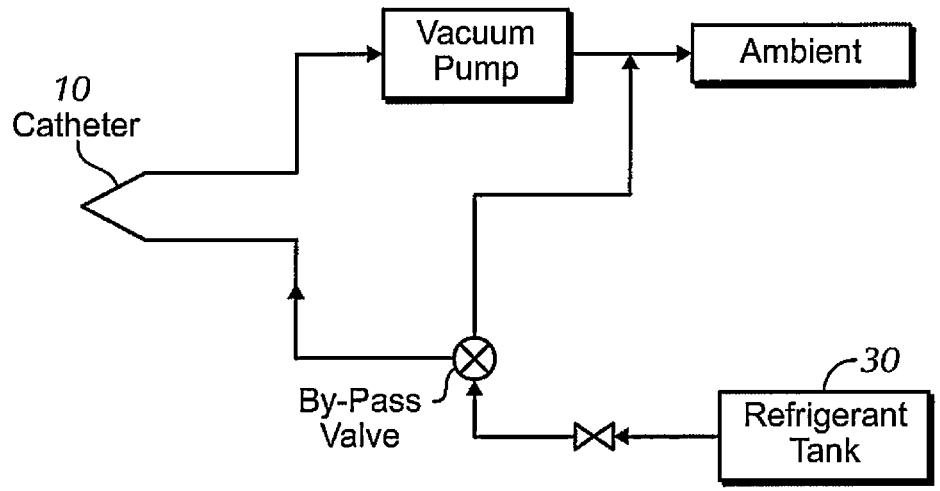
Figure 10:
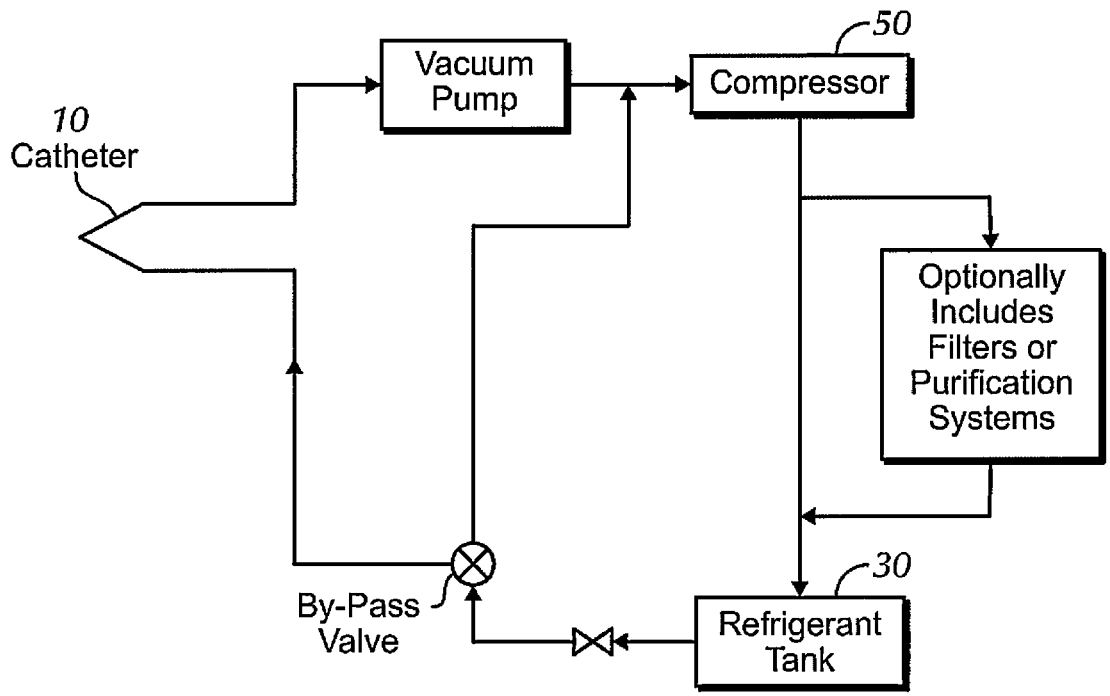

Now in reference to FIG. 5, a flow chart of non-limiting logic in accordance with present principles is shown. Beginning at block 64, a biocompatible substance in accordance with present principles is disposed between an inner sleeve and an outer sleeve of a catheter in accordance with present principles. At block 66, the space containing the biocompatible substance is enclosed such that no biocompatible substance may escape from the space in which it is disposed, except, in some embodiments, through the proximal end only. Moving to block 68, the biocompatible substance in the catheter is frozen by, e.g., conducting an initial circulation of the refrigerant through the catheter, although in some embodiments this step is omitted to ensure the catheter retains sufficient flexibility for placement in the patient's vasculature. Then at block 70, the catheter with the biocompatible substance is positioned/placed into a patient. Concluding at block 72, a refrigerant is circulated in the inner sleeve to remove heat from the biocompatible substance on the opposite side of the inner sleeve.

Note that in addition to the refrigerant sensor, a sensor 100 (FIG. 3) such as a temperature sensor or optical sensor may be disposed in the chamber holding the biocompatible substance to generate a signal representing the temperature or state (i.e., frozen or liquid) thereof. If the biocompatible substance remains frozen the temperature should be at the freezing point of the biocompatible substance. A second temperature signal can be patient temperature as measured by another probe or a temperature sensor external to the catheter.

Thus the biocompatible substance chamber is filled and the catheter advanced into patient, circulating refrigerant to freeze the biocompatible substance until patient target temperature as sensed by the external sensor is reached. The internal temperature signal from the temperature sensor inside the chamber holding the biocompatible substance is monitored and if the temperature rises above the freezing point of the biocompatible substance prior to reaching patient target temperature, refrigerant is circulated in catheter to freeze the biocompatible substance. Once patient temperature reached, refrigerant is circulated only as needed to prevent a temperature rise in the biocompatible substance, or the catheter may be removed from the patient altogether.

While the particular PATIENT TEMPERATURE CONTROL CATHETER WITH OUTER SLEEVE COOLED BY INNER SLEEVE is herein shown and described in detail, it is to be understood that the subject matter which is encompassed by the present invention is limited only by the claims.

What is claimed is:

1. A catheter, comprising:
   an inner sleeve through which refrigerant can circulate to and from a source of refrigerant;
   an outer sleeve surrounding the inner sleeve including a distal end thereof and filled with a frozen biocompatible substance, the refrigerant being separated from the biocompatible substance by one or more walls of the inner sleeve such that when the catheter is disposed in a patient, the refrigerant is isolated from the patient by both the inner sleeve and the frozen biocompatible substance, the refrigerant circulable through the catheter when the catheter is positioned in the patient to maintain the biocompatible substance frozen as heat is transferred from the patient to the biocompatible substance; and
   at least one refrigerant sensor positioned between the inner and outer sleeves, the refrigerant sensor communicating with a control system engaged with the catheter and responsive to detecting refrigerant between the inner and outer sleeves, generating a signal to the control system for causing the control system to activate an audible and/or visual alarm.

2. The catheter of claim 1, comprising the refrigerant, wherein the refrigerant is a fluorinated hydrocarbon.

3. The catheter of claim 1, wherein the frozen biocompatible substance is saline.

4. The catheter of claim 1, wherein the inner sleeve is cylindrical.

5. The catheter of claim 1, wherein the inner sleeve has an opening juxtaposed with a proximal end of the inner sleeve and a closed distal end opposite the proximal end such that refrigerant may enter the inner sleeve only through the proximal end and cannot pass through the distal end.

6. The catheter of claim 1, wherein the inner and outer sleeves are coaxial with each other.

7. A system, comprising:
- a catheter for cooling a patient, wherein the catheter has an inner sleeve through which refrigerant from a source of refrigerant can circulate to and from the source of refrigerant;
- wherein the catheter has an outer sleeve surrounding the inner sleeve including a distal end thereof and filled with a biocompatible substance;
- wherein the refrigerant can circulate through the catheter to maintain the biocompatible substance below the freezing point of the biocompatible substance as heat is transferred to the biocompatible substance; and
- at least one fluorinated hydrocarbon sensor positioned between the inner and outer sleeves of the catheter, the fluorinated hydrocarbon sensor configured for communicating with a control system.

8. The system of claim 7, wherein the biocompatible substance is frozen and the outer sleeve extends the length of the inner sleeve.

9. The system of claim 7, wherein the inner sleeve of the catheter has an opening juxtaposed with a proximal end of the inner sleeve and the distal end opposite the proximal end such that refrigerant may enter the inner sleeve only through the proximal end and cannot pass through the distal end.

10. The system of claim 7, further comprising at least one control system engageable with the catheter and configured for, responsive to a signal from the fluorinated hydrocarbon sensor, generating a signal to activate an audible and/or visual alarm.

11. System comprising:
- at least one catheter including an inner chamber configured to receive refrigerant therein and an outer chamber surrounding the inner chamber and configured to hold a biocompatible fluid therein, such that the biocompatible fluid can exchange heat with the refrigerant; and
- a control system configured for receiving a patient temperature signal and responsive to the patient temperature control signal, selectively circulating refrigerant in the inner chamber.

12. The system of claim 11, comprising a refrigerant in the inner chamber and a biocompatible fluid in the outer chamber.

13. The system of claim 11, comprising a patient temperature sensor configured to communicate with the control system.

* * * * *